United States Patent
Liang et al.

(10) Patent No.: US 6,270,221 B1
(45) Date of Patent: Aug. 7, 2001

(54) APPARATUS AND METHOD FOR MEASURING VISION DEFECTS OF A HUMAN EYE

(75) Inventors: Junzhong Liang, Fremont, CA (US); James H. Burkhalter, Orlando, FL (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

(21) Appl. No.: 09/665,748

(22) Filed: Sep. 20, 2000

Related U.S. Application Data

(63) Continuation of application No. 09/274,672, filed on Mar. 24, 1999, now abandoned.
(60) Provisional application No. 60/097,086, filed on Aug. 19, 1998.

(51) Int. Cl.[7] .......................................................... A61B 3/10
(52) U.S. Cl. ............................................................ 351/221
(58) Field of Search ..................................... 351/205, 211, 351/212, 219, 221, 246, 247; 600/108; 607/7, 10, 11, 12, 13, 17, 130, 88, 89; 128/898

(56) References Cited

U.S. PATENT DOCUMENTS

| 3,880,501 | 4/1975 | Munnerlyn . |
| 4,069,823 | 1/1978 | Isakov et al. . |

(List continued on next page.)

FOREIGN PATENT DOCUMENTS

| 42 22 395 | 1/1994 | (DE) . |
| 0 697 611 A2 | 2/1996 | (EP) . |
| 0 697 611 A3 | 2/1996 | (EP) . |
| 5-146409 | 6/1993 | (JP) . |
| 6-327634 | 11/1994 | (JP) . |

(List continued on next page.)

OTHER PUBLICATIONS

Liang, Junzhong, A New Method to Precisely Measure the Wave Aberrations of the Human Eye with a Hartmann–Shack Wavefront Sensor, Inaugural Dissertation, Dec. 1991, pp. 1–115, Heidelberg, Germany.

Pulianto, et al., "High–Speed Photography of Excimer Laser Ablation of the Cornea," *Arch Ophithalmol*, vol. 105, Sep. 1987, pp. 1255–1259.

Liang, et al., "Objective Measurement of Wave Aberrations of the Human Eye with the Use of a Hartmann–Shack Wave–front Sensor," *J. Opt. Soc. Am. A*, vol. 11, No. 7, Jul. 1994, pp. 1949–1957.

Wu, "Supernormal Vision, a Focus on Adaptive Optics Improves Images of the Eye and Boosts Vision," *Science News*, vol. 152, Nov. 15, 1997, pp. 312–313.

(List continued on next page.)

*Primary Examiner*—George Manuel
(74) *Attorney, Agent, or Firm*—Jeffrey S. Schira

(57) ABSTRACT

Optical characteristics of optical systems, such as the eye, are measured including vision defects of the eye using a collimated beam from a diode laser focused onto the anterior surface of the cornea of the eye for providing a finite source of secondary radiation on the retina of the eye, the image of which is close to a desired diffraction limited spot. The secondary radiation is reflected back from the retina as a reflected wavefront of radiation that passes through the eye and is directed onto a wavefront analyzer where distortions associated with the reflected wavefront are measured. By focusing on the cornea through a long focal length lens and thus converging the beam through a small angle, as opposed to typically focusing a collimated light onto the retina, the need for lenses or lens combinations, and the time required to adjust such to accommodate the differing vision of each patient is eliminated.

76 Claims, 3 Drawing Sheets

U.S. PATENT DOCUMENTS

| | | |
|---|---|---|
| 4,523,821 | 6/1985 | Lang et al. . |
| 4,579,430 | 4/1986 | Bille . |
| 4,632,528 | 12/1986 | Yoshino et al. . |
| 4,669,466 | 6/1987 | L'Esperance . |
| 4,688,941 | 8/1987 | Philbert . |
| 4,702,245 | 10/1987 | Schröder et al. . |
| 4,718,418 | 1/1988 | L'Esperance, Jr. . |
| 4,721,379 | 1/1988 | L'Esperance . |
| 4,729,372 | 3/1988 | L'Esperance, Jr. . |
| 4,750,818 | 6/1988 | Cochran . |
| 4,764,930 | 8/1988 | Bille et al. . |
| 4,838,679 | 6/1989 | Bille . |
| 4,848,340 | 7/1989 | Bille et al. . |
| 4,881,808 | 11/1989 | Bille et al. . |
| 4,901,718 | 2/1990 | Bille et al. . |
| 4,907,586 | 3/1990 | Bille et al. . |
| 4,941,093 | 7/1990 | Marshall et al. . |
| 4,972,836 | 11/1990 | Schenck et al. . |
| 4,988,348 | 1/1991 | Bille . |
| 4,991,953 | 2/1991 | Pflibsen et al. . |
| 5,026,977 | 6/1991 | Hubbard, Jr. . |
| 5,062,702 | 11/1991 | Bille . |
| 5,106,183 | 4/1992 | Yoder, Jr. . |
| 5,114,628 | 5/1992 | Höfer . |
| 5,139,022 | 8/1992 | Lempert . |
| 5,147,352 | 9/1992 | Azema et al. . |
| 5,159,361 | 10/1992 | Cambier et al. . |
| 5,177,511 | 1/1993 | Feuerstein et al. . |
| 5,184,157 | 2/1993 | Ichihashi et al. . |
| 5,196,006 | 3/1993 | Klopotek et al. . |
| 5,198,845 | 3/1993 | Triller . |
| 5,202,709 | 4/1993 | Ischihashi et al. . |
| 5,214,456 | 5/1993 | Gersten . |
| 5,221,834 | 6/1993 | Lisson et al. . |
| 5,229,889 | 7/1993 | Kittell . |
| 5,233,174 | 8/1993 | Zmek . |
| 5,243,367 | 9/1993 | Spellitz . |
| 5,246,435 | 9/1993 | Bille et al. . |
| 5,258,791 | 11/1993 | Penney et al. . |
| 5,263,950 | 11/1993 | L'Esperance, Jr. . |
| 5,279,611 | 1/1994 | McDonnell et al. . |
| 5,293,871 | 3/1994 | Reinstein et al. . |
| 5,298,971 | 3/1994 | Huang et al. . |
| 5,307,097 | 4/1994 | Baker . |
| 5,324,281 | 6/1994 | Muller . |
| 5,334,190 | 8/1994 | Seiler . |
| 5,339,121 | 8/1994 | Shimmick et al. . |
| 5,360,424 | 11/1994 | Klopotek . |
| 5,395,356 | 3/1995 | King et al. . |
| 5,404,884 | 4/1995 | Lempert . |
| 5,410,376 | 4/1995 | Cornsweet et al. . |
| 5,411,501 | 5/1995 | Klopotek et al. . |
| 5,423,801 | 6/1995 | Marshall et al. . |
| 5,437,658 | 8/1995 | Muller et al. . |
| 5,439,462 | 8/1995 | Bille et al. . |
| 5,442,412 | 8/1995 | Frey et al. . |
| 5,452,031 | 9/1995 | Ducharme . |
| 5,461,212 | 10/1995 | Seiler et al. . |
| 5,473,392 | 12/1995 | Klopotek . |
| 5,474,548 | 12/1995 | Knopp et al. . |
| 5,475,452 | 12/1995 | Kuhn et al. . |
| 5,491,524 | 2/1996 | Hellmuth et al. . |
| 5,493,391 | 2/1996 | Neal et al. . |
| 5,502,518 | 3/1996 | Lieberman . |
| 5,505,723 | 4/1996 | Muller . |
| 5,507,741 | 4/1996 | L'Esperance, Jr. . |
| 5,512,965 | 4/1996 | Snook . |
| 5,512,966 | 4/1996 | Snook . |
| 5,521,657 | 5/1996 | Klopotek . |
| 5,548,354 | 8/1996 | Kasahara et al. . |
| 5,556,395 | 9/1996 | Shimmick et al. . |
| 5,563,709 | 10/1996 | Poultney . |
| 5,570,142 | 10/1996 | Lieberman . |
| 5,581,347 | 12/1996 | Le Saux et al. . |
| 5,592,246 | 1/1997 | Kuhn et al. . |
| 5,629,765 | 5/1997 | Schmutz . |
| 5,632,282 | 5/1997 | Hay et al. . |
| 5,632,742 | 5/1997 | Frey et al. . |
| 5,673,096 | 9/1997 | Dorsel et al. . |
| 5,684,545 | 11/1997 | Dou et al. . |
| 5,711,762 | 1/1998 | Trokel . |
| 5,722,427 | 3/1998 | Wakil et al. . |
| 5,735,283 | 4/1998 | Snook . |
| 5,735,843 | 4/1998 | Trokel . |
| 5,740,803 | 4/1998 | Gray et al. . |
| 5,757,463 | 5/1998 | Kohayakawa . |
| 5,777,719 | 7/1998 | Williams et al. . |
| 5,784,146 | 7/1998 | Nanjo et al. . |
| 5,785,704 | 7/1998 | Bille et al. . |
| 5,822,035 | 10/1998 | Bille . |
| 5,825,746 | 10/1998 | Lee . |
| 5,841,511 | 11/1998 | D'Souza et al. . |
| 5,847,804 | 12/1998 | Sarver et al. . |
| 5,861,955 | 1/1999 | Gordon . |
| 5,864,381 | 1/1999 | Neal et al. . |
| 5,920,373 | 7/1999 | Bille . |
| 5,936,720 | 8/1999 | Neal et al. . |
| 5,943,117 | 12/1999 | Van De Velde . |
| 5,949,521 * | 9/1999 | Williams ............................. 351/246 |
| 5,963,300 | 10/1999 | Horwitz . |
| 5,966,197 | 10/1999 | Yee . |
| 6,007,024 | 12/1999 | Fahrenkrug et al. . |
| 6,095,651 | 8/2000 | Williams et al. . |

FOREIGN PATENT DOCUMENTS

| | | |
|---|---|---|
| WO 87/05205 | 9/1987 | (WO) . |
| WO 87/06478 | 11/1987 | (WO) . |
| WO 92/01417 | 2/1992 | (WO) . |
| 95/28989 | 11/1995 | (WO) . |
| WO 98/27863 | 7/1998 | (WO) . |

OTHER PUBLICATIONS

Dreher, et al., "Active Optical Depth Resolution Improvement of the Laser Tomographic Scanner," *Applied Optics*, vol. 28, No. 4, Feb. 1989, pp. 804–808.

Geary, "Appendix 1.1—Basic Geometrical Optics, Chapter 6—Indirect Wavefront Measurement, Part II," and "Chapter 7—Wavefront Sensor Characterization & Calibration," *Introduction to Wavefront Sensors*, May 1995, pp. 10–11, 89–103, 105–109.

"Scientists Snap Sharpest Pictures of Living Human Retina," http://www.rochester.edu/pr/releases/opt/will.htm, Oct. 3, 1994.

The Applied Optics Group, "Shack Hartmann Sensors," http://op.ph.ic.ac.uk/ao/sh sense.html, Jun. 4, 1996, pp. 1–3.

The Applied Optics Group, "Results from UKIRT," http://op.ph.ic.ac.uk/ao/ukirt res.html, Feb. 22, 1995, pp. 1–2.

The Applied Optics Group, "Astronomical Imaging Through Turbulence: An Overview," http://op.ph.ic.ac.uk/ao/overview.html, Jun. 4, 1996, pp. 1–4.

.eESA, WFS, "Wave Front Sensor," http://esapub.esrin.esa.it/pointtotest/test251.html, May 23, 1997, pp. 1–2.

Williams, "Limits of Human Vision," http://www.cvs.rochester.edu/people/d williams/d williams.html, Dec. 30, 1998, pp. 1–4.

"Extensions of Low–Cost Adaptive Optics: Imaging of Space–Objects, the Retina, and Power Projection," Industrial Sensors and Actuators, dated Dec. 1993 (actual publication date, if any, unknown), pp. 1, 10, and 15.

Labjuhn, et al., Astigmatismuskorrektur durch Laser-thermokeratoplastik (LTK)—Ein Ansatz für die Korrektur des hohen Astigmatismus nach Perforierender Kerotoplastik, *Contactologia 18D* (1996), pp. 175–183.

Cohen, et al., "Assessment of the Power and Height of Radial Aspheres Reported by a Computer–assisted Keratoscope," *American Journal of Ophthalmology*, vol. 119, vol. No. 6, Nov. 30, 1994, pp. 723–732.

Corbett, et al., "The Topography of the Normal Cornea," *Eur J Implant Ref Surg.*, vol. 6, Oct., 1994, pp. 286–297.

Maeder, et al., "Accurate 3D Corneal Surface Measurement Using an Automated Mapping Approach," SPIE, vol. 2434, 1995, pp. 328–334.

Salmon, et al., "Comparison of Elevation, Curvature, and Power Descriptors for Corneal Topographic Mapping," *Optometry & Vision Science*, vol. 72, No. 11, 1195, pp. 800–808.

Pavlopoulous, et al, "The Effect of Artificial Tears on Computer–assisted Corneal Topography in Normal Eyes and After Penetrating Keratoplasty," *American Journal of Ophthalmology*, vol. 119, Jun. 1995, pp. 712–722.

Roberts, "Characterization of the Inherent Error in a Spherically–Biased Corneal Topography System in Mapping a Radially Aspheric Surface," *Journal of Refractory & Corneal Surgery*, vol. 10, Mar./Apr. 1994, pp. 103–111.

Thornton, "Clinical Evaluation of Corneal Topography," *J. Cataract Refract. Surg.*, vol. 19, Supplement 1993, pp. 198–202.

Rabinowitz, et al., "Computer–assisted Corneal Topography in Keratoconus," *Refractive & Corneal Surgery*, vol. 5, Nov./Dec. 1989, pp. 400–408.

Wilson, et al., "Accuracy and Precision of the Corneal Analysis System and the Topographic Modeling System," *Cornea*, vol. 11, No. 1, 1992, pp. 28–35.

Bogan, et al., Computer–assisted Videokeratography of Corneal Topography After Radial Keratotomy, *Arch. Ophthalmol.*, vol. 109, Jun. 1991, pp. 834–841.

Bogan, et al., "Classification of Normal Corneal Topography Based on Computer–assisted Videokeratography," *Arch Ophthalmol.*, vol. 108, Jul. 1990, pp. 945–949.

Reidy, et al., "The Corneal Topography of Epikeratophakia," *Refractive & Corneal Surgery*, vol. 6, Jan./Feb. 1990, pp. 26–31.

Dingeldein, et al., "The Topography of Normal Corneas," *Arch Ophthalmol*, vol. 107, Apr. 1989, pp. 512–518.

McDonnell, et al., "Topographic Analysis of Visual Acuity After Radial Keratotomy," *American Journal of Ophthalmology*, vol. 106, No. 6, Dec. 1988, pp. 692–695.

McDonnell, et al., "Corneal Topographic Changes After Radial Keratotomy," *Ophthalmology*, vol. 96, No. 1, Jan. 1989, pp. 45–49.

Kiely, et al., "The Mean Shape of the Human Cornea," *Optica Acta*, vol. 29, No. 8, 1982, pp. 1027–1040.

Bafna, et al., "Corneal Power Calculated by the Paraxial Formula and Snell's Law in Normal Corneas," *Investigative Ophthalmology & Visual Science*, vol. 37, No. 3, Feb. 1996, Poster No. 2589.

Matallana, et al, "3–D Video Corneal Topography True Elevation Mapping," *Investigative Ophthalmology & Visual Science*, vol. 37, No. 3, Feb. 1996, Poster No. 2590.

Aoyama, et al, "Quantitative Evaluation of Corneal Astigmatism Using Computer Corneal Topography and Newly Developed Software," *Investigative Ophthalmology & Visual Science*, vol. 37, No. 3, Feb. 1996, Poster No. 2591.

Celikkol, et al, "Neural Network Analysis of Videokeratography Following Excimer Laser Photorefractive Keratectomy," *Investigative Ophthalmology & Visual Science*, vol. 37, No. 3, Feb. 1996, Poster No. 2592.

Walsh, et al., "Objective Technique for the Determination of Monochromatic Aberrations of the Human Eye," *J. Pot. Soc. Am. A*, vol. 1, No. 9, Sep. 1984, pp. 987–992.

Williams, et al., "Adaptive Optics for High Resolution Retinal Imaging," *Investigative Ophthalmology & Visual Science*, vol. 37, No. 3, Feb. 1996, p. 1055.

Charman, "Wavefront Aberration of the Eye: A Review," *Optometry and Vision Science*, vol. 68, No. 8, pp. 547–583.

Bartsch, et al., "Resolution Improvement in Confocal Scanning Laser Tomography of the Human Fundus," 1994 *Technical Digest Series*, vol. 2 (Optical Society of America, Washington, D. C.), 1994, pp. 134–137.

Bille, et al., "Scanning Laser Tomography of the Living Human Eye," *Noninvasive Diagnostic Techniques in Ophthalmology*, Chapter 28, edited by Masters, B.R., Springer–Verlag, 1990, pp. 528–547.

Dreher, et al., "Active Optical Depth Resolution Improvement of the Laser Tomographic Scanner," *Applied Optics*, vol.28, No. 4, Feb. 1989, pp. 804–808.

* cited by examiner

APPARATUS AND METHOD FOR MEASURING VISION DEFECTS OF A HUMAN EYE

CROSS-REFERENCE TO RELATED APPLICATION

This Application is a continuation of and hereby incorporates by reference application Serial No. 09/274,672, filed Mar. 24, 1999 now abandoned, which itself claims priority to Provisional Application having Ser. No. 60/097,086, filed on Aug. 19, 1998 for "Apparatus and Method for Measuring Vision Defects of a Human Eye" all of which are commonly owned with the instant application.

BACKGROUND OF INVENTION

1. Field of Invention

The invention relates generally to optical aberration measurements and correction, and in particular to projection techniques in the objective measurement and correction of the human eye using a wavefront sensor.

2. Description of Background Art

There has been and continues to be a need to provide a person with improved visual acuity. Remodeling of the cornea using refractive laser surgery or intra-corneal implants, adding synthetic lenses using intra-ocular lens implants or precision ground contact lenses or eye glasses provide known solutions. Further, it is known to correct vision astigmatically by surgical modification of myopic or hyperopic astigmatism through laser keratoplasty, keratomileusis or photorefractive keratectomy. Laser sources are used to erode or ablate surfaces of the eye, typically reshaping the cornea. Prior to and during such surgery, precise measurements must be made to determine required surgical corrections.

The imprecise measurement technique of placing lenses of known refractive power anterior to the cornea and asking a patient which lens or lens combination provides the clearest vision has been improved with the use of autorefractometers, as described in U.S. Pat. No. 5,258,791 to Penny et al., or with the use of wavefront sensors as described by Liang et al. in "Objective Measurement of Wave Aberrations of the Human Eye with the Use of a Hartmann-Shack Wave-Front Sensor," Journal of the Optical Society of America, Vol. 1, No. 7, July 1994, p.p 1949–1957, by way of examples. Penny '791 discloses the use of autorefractometer measurements for determining the appropriate corneal surface reshaping to provide emmetropia, a condition of a normal eye when parallel rays are focused exactly on the retina and vision is optimum. Spatially resolved refraction data, in combination with measured existing surface contour of the anterior surface of the eye, enable a calculation of a detailed spatially resolved new contour which provides corrected vision. It would be an improvement in this art if such vision correction could be made without the need for this contour data, and further without the need for feedback from the patient regarding an appropriate lens. Liang et al. disclose the use of a Hartmann-Shack wavefront sensor to measure ocular aberrations by measuring the wavefront emerging from the eye by retinal reflection of a focused laser light spot on the retina's fovea. A parallel beam of laser light passes through beam splitters and a lens pair which brings the beam to a focus point on the retina by the optics of the eye. Possible myopia or hyperopia of the tested eye is corrected by movement of a lens within the lens pair. The focused light on the fovea is then assumed to be diffusely reflected and acts as a point source located on the retina. The reflected light passes through the eye and forms a distorted wavefront in front of the eye that results from the ocular aberrations. The aberrated wavefront is then directed to the wavefront sensor.

A point source of radiation on the retina would be ideal for such measurements. However, when the perfect eye receives a collimated beam of light, the best possible image on the retina is a diffraction limited spot. As illustrated by way of example, with Penny et al. and Liang et al., discussed above, and typical for those of skill in the art, parallel or collimated beams are used with the optics of the eye being measured to achieve this diffraction limited spot for such objective measurements. To do so requires that a setup for each patient include a corrective lens or lens combination and adjustments thereto for accommodating that patient's specific visual acuity. Providing a corrective or lens combination, as well as setting up for their use becomes cumbersome, time consuming, and requires additional expense. Eliminating the need for such corrective optics is desirable and eliminates a variable within optical measurement systems that typically include many variables. Further, there is a need for providing optical characteristics of an eye without requiring feedback from the patient. By way of example, the patient may be a wild or domestic animal, living or dead.

SUMMARY OF INVENTION

In view of the foregoing background, it is therefore an object of the present invention to provide a refraction measurement system that easily accommodates the measurement of vision characteristics of the eye, even in the presence of finite refractive errors. It is another object to improve upon the time required for a patient to be in a fixed position during examination, while at the same time providing a useful source of light on the retina of the eye to be measured regardless of the characteristics of the eye of that patient or other patients to be examined. It is further an object to measure such characteristics without requiring patient or operator feedback.

These and other objects, advantages and features of the present invention are provided by a method aspect of the invention for measuring optical characteristics of an optical system including the focusing of an optical beam proximate an anterior surface of the optical system for placing a finite source of secondary radiation on a focal surface of the optical system, which secondary radiation is emitted from the focal surface as a reflected wavefront of radiation that passes through the optical system, projecting the reflected wavefront onto a wavefront analyzer, and measuring characteristics of the optical system associated with the reflected wavefront. In a preferred embodiment, the method includes measuring defects of the eye which includes the steps of focusing an optical beam onto an anterior surface of the eye for providing a finite source of secondary radiation on the retina of the eye, which secondary radiation is emitted from the retina as a reflected wavefront of radiation that passes through the eye; directing the reflected wavefront onto a wavefront analyzer; and measuring distortions associated with the reflected wavefront. A preferred embodiment of the invention includes the step of focusing the projected optical beam on the anterior surface of the cornea.

An apparatus for effectively performing such measurements includes focusing means for focusing an optical beam onto an anterior surface of the optical system or eye for providing a finite secondary radiation source on the focal surface, or retina of the eye, which finite secondary radiation source is emitted from the retina as a reflected wavefront of radiation that passes through the eye, directing means for directing the reflected wavefront onto a wavefront analyzer, and a wavefront analyzer for measuring distortions associated with the reflected wavefront. In one preferred embodiment of the present invention, a laser beam is focused onto the surface of the cornea with a long focal length lens which converges the beam through a small angle for passing through the iris of the eye and providing a finite secondary radiation source on the retina of the eye, which finite secondary radiation source is emitted from the retina through the optics of the eye as the wavefront to be measured.

BRIEF DESCRIPTION OF DRAWINGS

A preferred embodiment of the invention as well as alternate embodiments are described by way of example with reference to the accompanying drawings in which.

DETAILED DESCRIPTION OF PREFERRED EMBODIMENTS

The present invention will be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
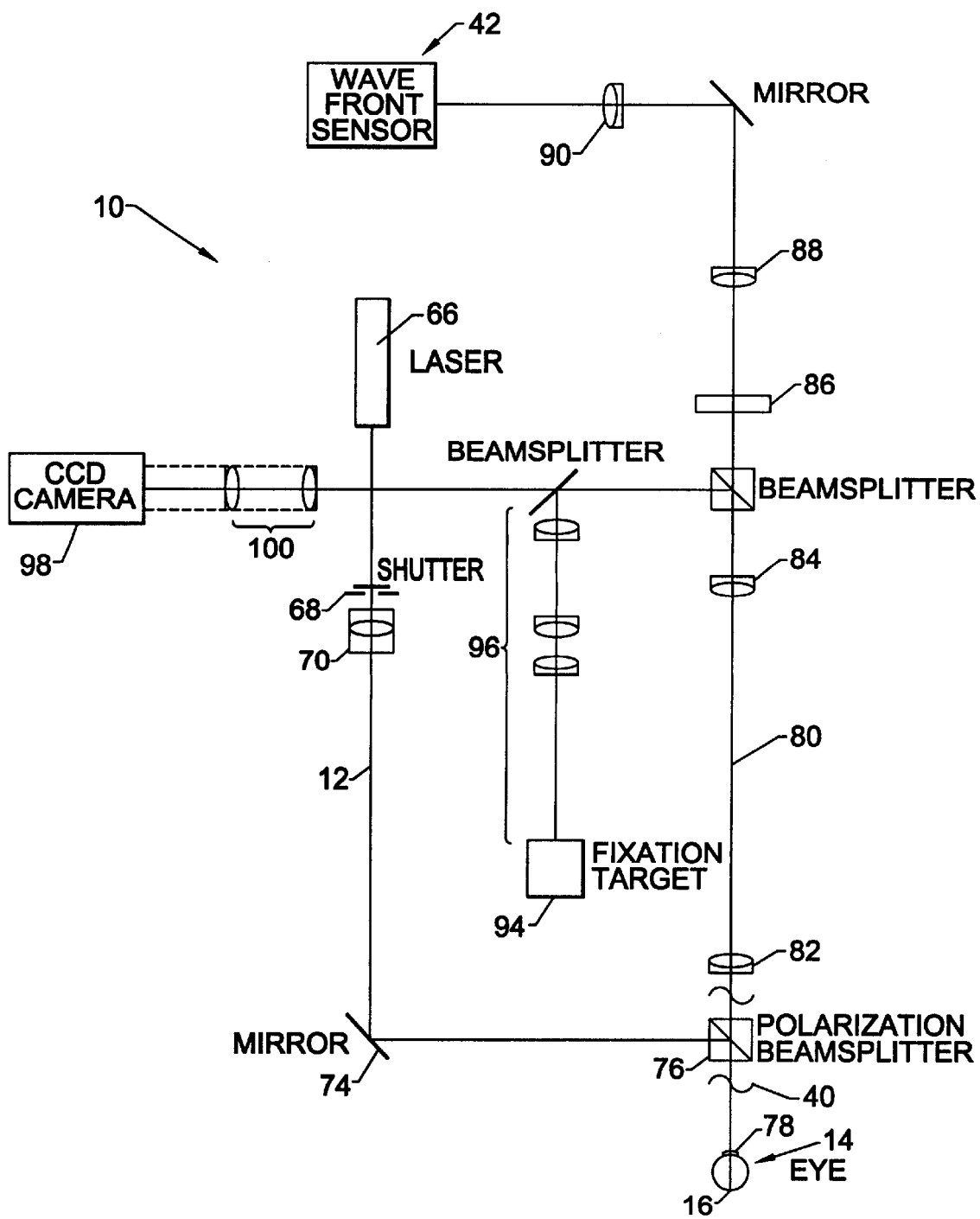
FIG. 1 is a diagrammatic illustration of an apparatus for measuring visual defects of an eye, according to the present invention.

A preferred embodiment of a measurement apparatus 10 of the present invention is herein initially described with reference to the schematic diagram of FIG. 1. A projected beam 12 of optical radiation is directed into an eye 14 to be measured, so that a small area or measurable spot 16 is formed as a secondary radiation source in the foveal region of the retina 18 as illuminated with reference to FIG. 2. Specifically, the beam 12 is focused through a small angle 13 onto an anterior surface 20 of the eye 14, and in a preferred embodiment of the present invention, focused on an anterior corneal surface 22 of the cornea 24 for further projection through the iris 26 and lens 28 and onto the retina 18.

Figure 3A:
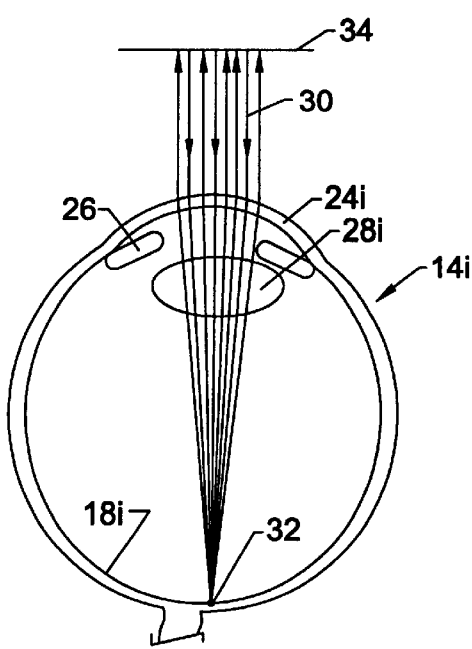
FIGS. 3A and 3B are diagrammatic illustrations of an ideal eye with perfect vision and an aberrated ideal eye, respectively.
Figure 3B:
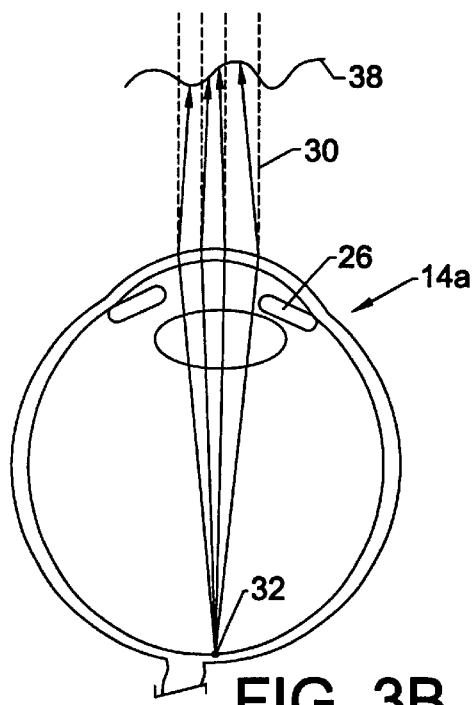

By way of further background, consider an "ideal" eye 14$i$ with ideal vision, as illustrated with reference to FIG. 3A. The ideal eye 14$i$, having the ideal cornea 24$i$ and ideal lens 28$i$ will focus a collimated beam of light, illustrated with arrows 30 to a point 32, as the secondary radiation source, on the ideal retina 18$i$. This point 32 would then be a point source of light which would be diffusely reflected back through the optics of the ideal eye 14$i$ as a sequence of plane waves 34. In actual fact, even an eye having perfect vision, as illustrated by way of example with reference to FIG. 4, will produce a diffraction limited illuminated area or spot 36, as the secondary radiation source, on the retina of the eye, under the best possible circumstances. In a typical eye, as illustrated with reference to FIG. 4, such a spot 36 is even larger, where most of the blurring will be due to finite aberrations found in typical eyes. By way of further example, in an aberrated eye 14$a$, if the point source 32 could be realized, distorted wavefronts 38 result as illustrated with reference to FIG. 3B. Having to deal with a series of distorted wavefronts 38 resulting from aberrations, and further dealing with a blurring of such distorted wavefronts 38 resulting from diffraction effects and the finite aberrations of the eye, results in a spot 36 source of light rather than a point 32 source. Such provides one of the challenges in measuring the visual defects or an eye.

Figure 4:
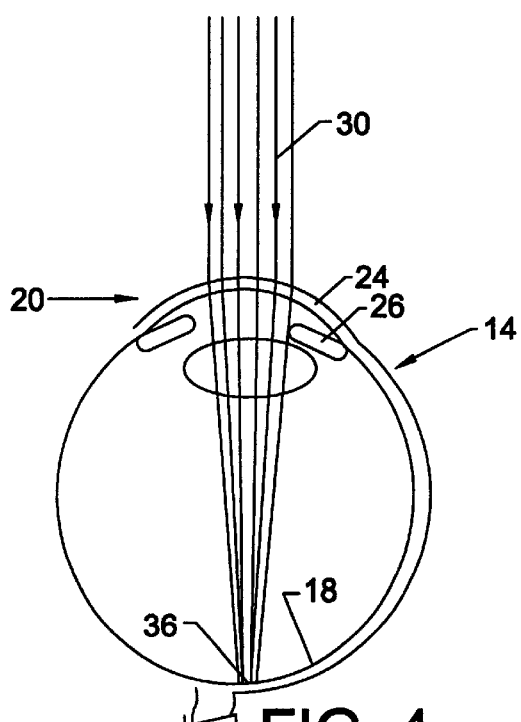
FIG. 4 is a diagrammatic illustration of an eye being measure with collimated light focused on the retina to a diffraction limited spot.

It is typical in the art of eye measurements to form a collimated beam and attempt to focus the collimated beam onto the retina, using lenses and lens combinations with the optics of the eye to produce the smallest possible spot 36, as earlier described with reference to FIG. 4. Lenses and focusing techniques typically take valuable time and include multiple attempts to focus a spot on the retina using various lenses and lens combinations to accommodate each unique vision of each patient being measured. With the present invention, and the understanding that most of the blurring results from the curvature of the cornea, the present invention eliminates the need to find lenses or lens combinations to minimize the size of the spot on the retina that is used as the secondary source of radiation.

Figure 2:
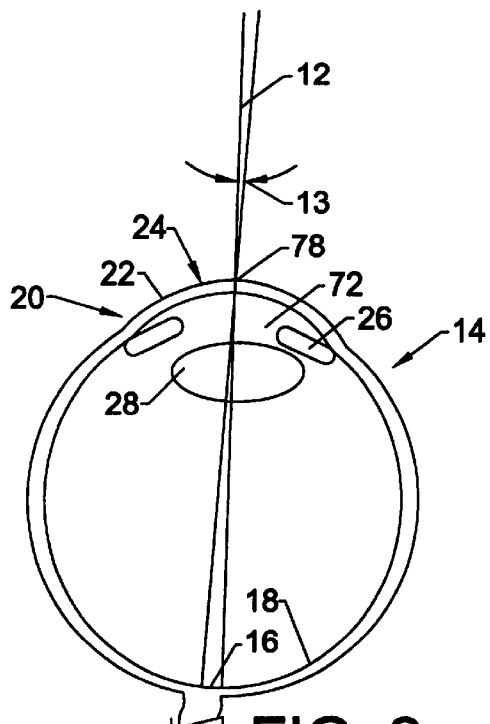
FIG. 2 is a diagrammatic illustration of a eye to be measured by the apparatus of the present invention.
Figure 5:
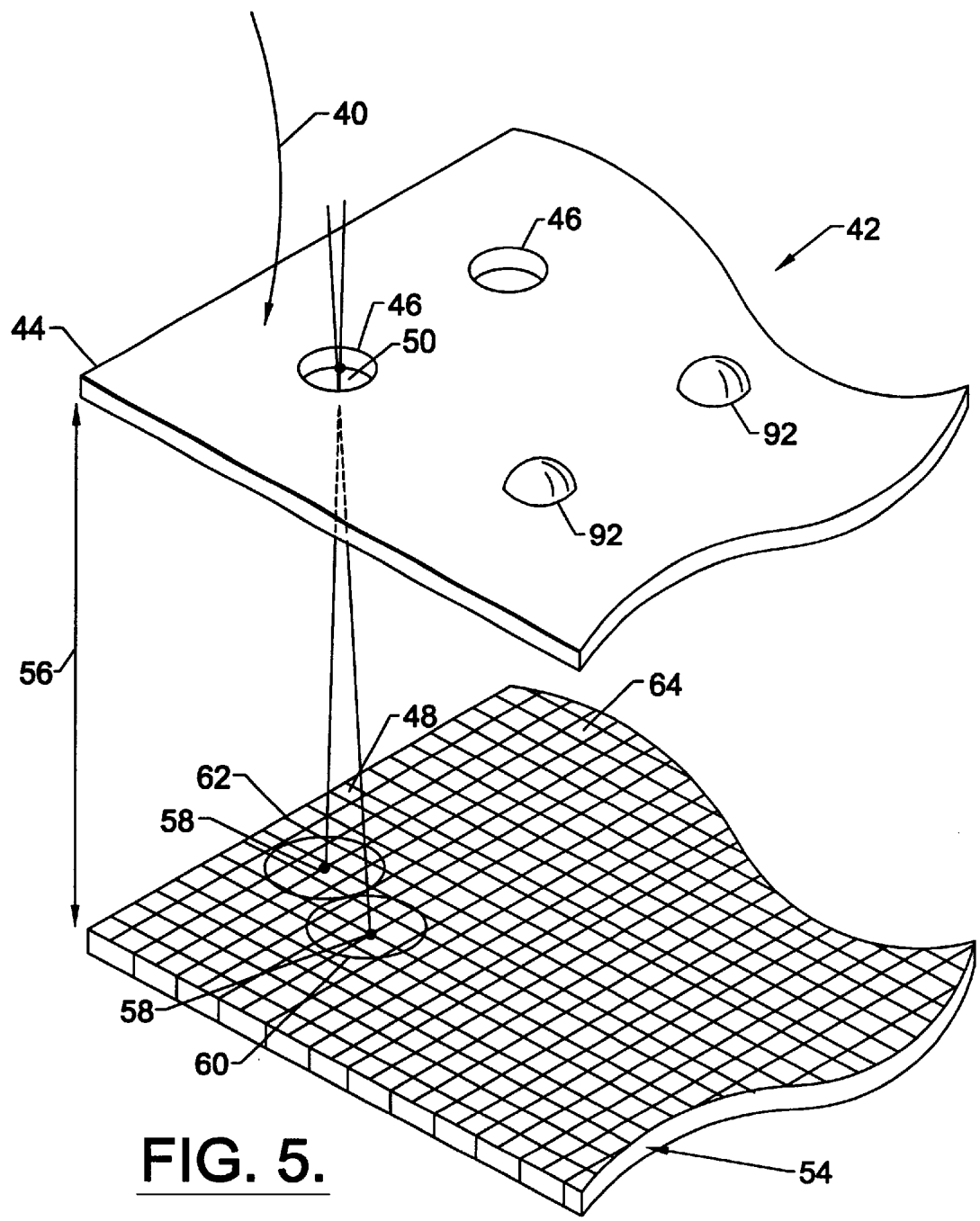
FIG. 5 is a partial perspective view of a pinhole imaging plate and detector plane of a wavefront sensor used in a preferred embodiment of the present invention.

With reference again to the embodiment described in FIGS. 1 and 2, the optical wavefronts 40 scattered from the retina 18 are transferred by a series of optical elements, which will be described in further detail later in this section, to a wavefront sensor 42, which wavefront sensor divides each incident wavefront into a group of "wavelets", referred to herein with numeral 50, using an opaque plate 44 having a planar array of apertures 46 as illustrated with reference to FIG. 5. Further, the wavefront sensor 42 records the position 48 at which each wavelet 50 passing through the aperture 46 strikes a detector plane 54 such as a charged coupled device (CCD) herein provided as one preferred embodiment, which plane is held a fixed small distance 56 behind the plate 44. The transverse displacement 58 of each wavelet 50 at the CCD detector plane 54 from a collimated light reference position 60 is then used to calculate a wavefront slope at each position of the apertures 46 within the planar aperture array. Alternate methods exist for using partial derivative data resulting from the measurements of the slope to calculate the wavefront 40. One acceptable approach is that used by Liang et al. in the aforementioned paper where the wavefront is closely approximated using Zernike polynomials.

At each position 48, a spot 62 typically extending beyond the light measurement area of one CCD element 64 is produced. As earlier discussed, blurring and a large diffraction limited spot make it difficult to make measurements. Thus, reducing blurring improves measurement at the detector plane 54.

With reference again to FIG. 1, in one preferred embodiment of the present invention, the apparatus 10 includes the projected beam 12 of linearly polarized light (S-component) emitted from a diode laser 66 (670 nm, 3 mW by way of example), which beam of light passes through an electromechanical shutter 68, which controls the duration of light exposure on the eye 14 of the patient, and in particular, the exposure of the retina 18 of the eye 14 illustrated with reference again to FIG. 2. It is expected that alternate sources of light, for example, non-coherent and non-polarized, as well as alternate light transmitting techniques will come to the mind of those skilled in the art without deviating from the teaching of the present invention. As herein described, the use of coherent light from a laser and polarization techniques are presently preferred. When the shutter 68 is open, the projected beam 12, collimated light from the diode laser 66, is directed by a long focal length lens 70 for focusing on the anterior surface 22 of the cornea 24 of the eye 14, as illustrated with reference yet again to FIG. 2, passing through the pupil 72 and lens 28 of the eye 14, and onto the retina 18 as the small measurable spot 16. In an alternate embodiment, lens 70 comprises a zoom lens for varying the focus and moving the focus location as desired. By focusing on the cornea 24, the measurement is minimally dependent on the curvature of the cornea. However, other locations proximate the corneal surface are acceptable.

While diffraction and various aberrations are present, the present invention avoids the aberration effects from the cornea which typically dominate. The lens 28 of the eye 14 contributes a relatively small aberration effect when compared to that of the cornea 24. Further, and with regard to the selection of lens 70, selecting a lens with a short focal length would provide a large angle 13, a well focused point 78 on the surface of the cornea 24, and less aberration effects from the cornea . However, a large angle 13 results in an undesirably larger retinal spot 16. The small angle 13 herein described provides a larger focus point 78 on the cornea 24 but the more desirable smaller spot 16 on the retina 18. The spot 16 will depend on the wavelength and starting point size and focal length of the lens 70 selected. In preferred embodiments of the present invention, lenses of approximate one half meter are selected for the lens 70. A 100 mm lens 70 has been effectively used.

In one preferred embodiment herein described, a mirror 74 and polarization beam splitter 76 direct the projected beam 12 to a focus 78 on the anterior surface 20 of the cornea 24. The projected beam 12, focused on the anterior surface 22 of the cornea 24, provides the measurable spot 16 as a light source (about 1.5 milliradians in visual space, by way of example) on the retina 18 of the eye 14 being measured, as illustrated with reference again to FIG. 2. Such a spot 16 provides an acceptable substitute for a diffraction limited spot typically sought.

By way of one preferred example of use, a method for measuring vision characteristics of the eye 14 includes directing the beam 12 through the long focal length lens 70 for providing the small angle 13, as illustrated with reference again to FIG. 2, about an optical path for passing the beam 12 through the pupil 72 of the eye 14. The beam 12 is first focused at a fixed location 78, without the eye or patient in place. All measuring equipment, the apparatus 10, is arranged without the patient in place and a convenient time prior to measuring. Then, the patient is positioned such that the anterior surface of the eye 14 of a patient is located at the fixed location 78 which in a preferred embodiment is the anterior surface of the cornea. This places a finite source of secondary radiation, the spot 16, as herein described, on the retina 18 of the eye 14, which provides light emitted from the retina 18 and through the pupil 72 as a reflected wavefront, the wavefront 38, described with reference to FIG. 3B. This wavefront 38 is directed onto the wavefront analyzer 42 for measurement.

In a preferred embodiment, the laser power reaching the eye is physically limited to a maximum of 7 $\mu$W. In measurements on human eyes using the apparatus 10, a laser pulse duration of 700 ms was used so that the total energy entering the eye would not exceed 4.9 $\mu$J. For comparison, according to the ANSI standard for direct "intrabeam" viewing, the maximum permissible exposure to a laser at the wavelength used is 530 $\mu$J. Thus, the probing laser energies effectively used in the present invention are two orders of magnitude below an "eye-safe" limit.

With reference again to FIG. 2, the light diffusely reflected by the retina 18 produces the wavefront 40, a distorted wavefront at the pupil plane due to the eye's aberrations. Diffuse reflection makes the returning light from the retina depolarized, containing not only an S-component but also a P-component of polarization light. The polarization beam splitter 76 in front of the eye 14 will only let the P-component pass through it and downstream to the wavefront sensor 42. The S-component is essentially totally reflected towards the diode laser 66. Because the light reflected by corneal surfaces preserves the polarization of the incoming beam (S-polarized), the corneal reflection is reflected by the beam splitter 76, and is thus rejected from the path 80 heading toward the wavefront sensor 42. The P-component of the aberrated wavefront 40 at the subject's pupil plane is then recreated by the combination of lens 82 and lens 84, at a trial lens plane 86 indicated as "Trial Lens" in FIG. 2. In one preferred embodiment, the diameter and the aperture of the lens 82 and lens 84 are 40 mm and 120 mm, respectively. The combination of lens 82 and lens 84 form an afocal image system with the eye's pupil 72 (the object plane) at the focal plane of the lens 82, and the image plane, trial lens 86, at the focal plane of the lens 84. Similarly, lens 88 and lens 90 also form an afocal image system with the possible trial lens 86 at the focal plane of the lens 88 and the lens combination at the image plane at the focal plane of the lens 90. The focal plane of the lens 90 is located at the plate 44 of the wavefront sensor 42, earlier described with reference to FIG. 5. In a preferred embodiment, Lens 4 has a diameter of 30 mm and a focal length of 80 mm. Lens 5 has a diameter of 40 mm and a focal length of 120 mm. With the apparatus 10, measured wavefront slopes leaving the eye 14 are recreated at the aperture plane 44, and magnified by a factor of 1.5. Magnification of the wavefront 40 at the detector plane 54 reduces the wavefront slopes by the same degree. This extends the dynamic range of eye aberrations over which the device can measure.

By way of further explanation about the trial lens location or plane 86, because the wavefront 40 leaving the eye 14 is recreated at this location 86 with unity magnification, a trial lens of known refractive power inserted at this point should exactly compensate for a prescribed refractive error. For example, a perfect five diopter spherical lens placed at this location should remove five diopters of spherical curvature from an incident wavefront, without altering other aberrations that may exist in the wavefront. The capability of inserting trial lenses at this location 86 extends the dynamic measurement range of the apparatus 10, without affecting wavefront analyzing capability.

In a preferred embodiment, and with reference again to FIG. 5, the aperture array 46 of the wavefront sensor 42 samples the incident wavefront 40 which forms focus spots 62 on the detector plane 54 This is repeated at the detector plane 54 for each aperture within the array 46. As a result, a localized direction of the wavefront 40 is determined for each of a plurality of wavelets 50 within the array. By way of example, the use of lenslets 92 (as an alternate embodiment of apertures 46 alone), with a focal length of 87 mm and a dimension of 0.768 mm, forms an aerial image of the retinal light source (the spot 16 described earlier with reference to FIG. 2) on the detector plane 54. If a plane wave, corresponding to an aberration-free eye, were measured, the lenslet 92 array would produce a regular array of focused spots on the image sensor. When the real eye 14 is measured, the wave aberration in the eye will displace the focus spot 62, described earlier with reference to FIG. 5, of each lenslet 92 from the reference position 60 to the measured position 50 in proportion to the local slopes of the wavefront 40. The wavefront sensor 42 measures the local wavefront slopes at an array of sampling locations across the pupil 72, from which the wavefront 40 itself can be reconstructed.

As illustrated again with reference to FIG. 1, in an alternate embodiment of te present inventive methods, a fixation target 94 may be used to insure that the patient is looking along the optical axis of the apparatus 10. The patient is asked to fixate on the target 94 located at the focal plane of a lens 96. By linearly moving the optics combination 96 of the fixation target 94, it is possible to provide the eye's spherical correction, and hence to make the fixation target 94 clearly visible to the subject. In one preferred use, the image of the fixation target 94 is intentionally under-corrected for each patient to ensure that the measured eye 14 is focused at infinity. By way of example, the fixation target consists of a dark cross-hair and a number of concentric circles on a white background that is back-illuminated by a tungsten lamp. The patient is asked to look at the center of the cross-hair. The position of the eye 14 in reference to the optical axis is recorded by CCD camera 98. This CCD camera 98 is conjugate, in effect coupled, to the eye's pupil 72 through a second lens combination 100, preferably mounted on the camera, and the lenses 82, 84. In one method of te present invention, the camera 98 is used to view the eye 14 for aligning the eye within the path of te beam 12 for assuring that the beam passes through the pupil 72. The camera 98 is also useful in an alternate embodiment of the present invention, for viewing the size of the spot 16 formed on the retina 18 as the user changes the focus point 78 through various anterior surface locations in obtaining an optimum size of the spot 16.

By way of further example of effective uses of the present invention, the earlier described Zernike coefficients of an eye, taken collectively, can be used as discriminating as fingerprints or DNA. The Zernike coefficients for a person might be used for identification of that person for permitting access to a confidential area, allowing funds to be distributed through an ATM, and the like. Further, the present invention allows eye measurements for a passive subject, such as in the examination of a corpse or sedated animal. The present invention is operable with human eyes, as herein described, as well as those of an animal, bird, or fish eyes, and in particular, non-biological focusing optical systems such as those found in cameras. The present invention is useful in developing optimized aspheric systems, where an aspheric element need to be designed last by observing and producing a single custom aspheric element that corrects the system. By way of example, the aspheric system may be designed on paper except for the correcting element, which would be developed experimentally using the present invention as herein described. The design of afocal systems such as a telescope, a searchlight, or a projector which require an added corrective focus element will benefit from the present invention.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and alternate embodiments are intended to be included within the scope of the appended claims.

That which is claimed is:

1. A method for measuring vision defects of an eye, the method comprising the steps of:

focusing an optical beam proximate an anterior surface of the eye, other than the retina, for placing a finite source of secondary radiation on the retina of the eye, which secondary radiation is emitted from the retina as a reflected wavefront of radiation that passes through the eye;

projecting the reflected wavefront onto a wavefront analyzer; and measuring distortions associated with the reflected wavefront.

2. The method according to claim 1, wherein the optical beam focusing step includes the step of focusing the optical beam on the anterior surface of the cornea.

3. The method according to claim 1, wherein the optical beam comprises a collimated laser beam.

4. The method according to claim 1, further comprising the steps of:

generating a linearly polarized, collimated beam of light; and positioning a long focal length lens for directing the collimated beam of light through the long focal length lens, and wherein the focusing step includes the step of converging the collimated light through a small angle to a focal point on the anterior surface of the eye.

5. The method according to claim 4, wherein the long focal length lens has a focal length between 0.5 and 5.0 meters in length.

6. The method according to claim 4, further comprising the step controlling an amount of optical beam energy delivered to the eye.

7. The method according to claim 1, wherein the distortion measuring step comprises the step of comparing the reflected wavefront received by the wavefront analyzer to a desirable wavefront received by the wavefront analyzer.

8. The method according to claim 1, wherein the distortion measuring step comprises the step of determining an optical path difference between a plane wave and the wavefront emanating from the retina of the eye.

9. The method according to claim 8, wherein the optical path difference results from a Zernike reconstruction of the wavefront.

10. The method according to claim 1, wherein the distortion measuring step comprises the steps of:

positioning an opaque plate having an aperture therein for transmitting a portion of the emitted wavefront therethrough;

placing a light-sensitive material downstream of and in spaced relation to the opaque plate for receiving the portion of the reflected wavefront projected as a finite image onto a first position of the light-sensitive material;

projecting the reflected wavefront onto the plate for placing a first finite image onto the light-sensitive material;

projecting a desirable wavefront onto the plate for placing a second finite image at a second location on the light-sensitive material; and measuring a difference between the first position and the second position.

11. The method according to claim 10, wherein the aperture comprises an aperture array and wherein the light-sensitive material comprises a CCD array.

12. The method according to claim 11, wherein the aperture array comprises a lens carried within each aperture for focusing light passing through the aperture onto the CCD array.

13. The method according to claim 1, further comprising the step of converting the measured distortions to an optical correction based on a deviation of the reflected wavefront from a desirable wavefront.

14. The method according to claim 13, wherein the desirable wavefront comprises a planar wavefront.

15. The method according to claim 14, wherein the polarizing step comprises the steps of:

providing a beam splitter;

passing the reflected wavefront having an S-component and a P-component polarization light through the beam splitter; and splitting the reflected wavefront by directing the P-component to the wavefront analyzer and the S-component therefrom.

16. The method according to claim 1, further comprising the step of polarizing the optical beam.

17. The method according to claim 1, further comprising the steps of:

positioning a fixation target for viewing;

focusing the eye on the fixation target for assuring that a patient whose eye is being measured is looking along a preferred direction.

18. The method according to claim 17, further comprising the step of adjusting the fixation target for ensuring that the measured eye is focused at infinity.

19. The method according to claim 1, further comprising the steps of:

viewing the pupil of the eye through a camera focused on the eye; and aligning the center of the eye along a beam path of the optical beam for confirming passage of the beam through the pupil of the eye.

20. A method for measuring vision characteristics of an eye, the method comprising the steps of:

projecting an optical beam through a sufficiently small angle about an optical path for passing the beam through the pupil of the eye and providing a finite spot on the retina of the eye;

focusing the optical beam proximate an anterior surface of the eye, other than the retina, for placing a finite source of secondary radiation on the retina of the eye, which secondary radiation provides light emitted from the retina and through the pupil as a reflected wavefront of radiation; and directing the reflected wavefront onto a wavefront analyzer for measuring distortions associated with the reflected wavefront.

21. The method according to claim 20, wherein the optical beam focusing step includes the step of focusing the optical beam on the anterior surface of the cornea.

22. The method according to claim 20, wherein the optical beam comprises a laser beam.

23. The method according to claim 20, further comprising the steps of:

generating a linearly polarized optical beam; and positioning a long focal length lens for directing the optical beam therethrough, and wherein the focusing step includes the step of directing the optical beam through the long focal length lens for providing the small angle in which to focus the optical beam.

24. The method according to claim 23, wherein the long focal length lens has a focal length of at least one half meter in length.

25. The method according to claim 20, further comprising the steps of:

providing a shutter within a beam path of the optical beam; and controlling an amount of optical beam energy delivered to the eye by operating the shutter from a closed position to an open position.

26. The method according to claim 20, further comprising the step of measuring an optical path difference between a desirable wavefront and the wavefront emanating from the retina of the eye.

27. The method according to claim 26, wherein the measuring step comprises the steps of:

positioning an opaque plate having an aperture array therein for transmitting a plurality of emitted wavelets of the emitted wavefront therethrough; and receiving finite images of the plurality of emitted wavelets on a light sensitive material downstream of and in spaced relation to the opaque plate.

28. The method according to claim 27, further comprising the steps of:

determining positions for each of the plurality of emitted wavelet finite images;

projecting the desirable wavefront onto the plate for placing a plurality of reference wavelets onto the light sensitive material;

determining positions for each of the plurality of reference wavelet finite images; and measuring a displacement between finite images, respectively, for the emitted wavelets and reference wavelets.

29. The method according to claim 28, further comprising the step of converting the displacement to an optical correction based on a difference between the reflected wavefront and the desirable wavefront.

30. The method according to claim 29, wherein the desirable wavefront comprises a planar wavefront.

31. The method according to claim 30, further comprising the steps of:

polarizing the optical beam;

passing the reflected wavefront through a beam splitter, wherein an S-component and a P-component of the polarized optical beam pass through the beam splitter; and splitting the reflected wavefront by directing the P-component to the wavefront analyzer and the S-component therefrom.

32. A method for measuring vision characteristics of an eye, the method comprising the steps of:

directing an optical beam through a long focal length lens for providing a sufficiently small angle about an optical path for passing the optical beam through the pupil of the eye;

focusing the optical beam at a fixed location;

positioning an anterior surface of the eye, other than the retina, of a patent at the fixed location for placing a finite source of secondary radiation on the retina of the eye, which secondary radiation provides light emitted from the retina and through the pupil as a reflected wavefront of radiation; and directing the reflected wavefront onto a wavefront analyzer for measuring the reflected wavefront.

33. The method according to claim 32, wherein the anterior surface comprises the anterior surface of the cornea.

34. The method according to claim 32, wherein the long focal length lens has a focal length of at least one half meter in length.

35. The method according to claim 32, further comprising the steps of:
providing a shutter within a beam path of the optical beam; and
controlling an amount of optical beam energy delivered to the eye by operating the shutter from a closed position to an open position.

36. The method according to claim 32, further comprising the step of measuring an optical path difference between a desirable wavefront and the wavefront emanating from the retina of the eye.

37. The method according to claim 32, further comprising the steps of:
polarizing the optical beam;
passing the reflected wavefront through a beam splitter, wherein an S-component and a P-component of the polarized optical beam pass through the beam splitter; and
splitting the reflected wavefront by directing the P-component to the wavefront analyzer and the S-component therefrom.

38. The method according to claim 32, wherein the positioning step comprises the steps of:
viewing the pupil of the eye through a camera focused on the eye; and
aligning the center of the eye along a beam path of the optical beam for confirming passage of the beam through the pupil of the eye.

39. A method for measuring vision characteristics of an eye comprising focusing an optical beam proximate an anterior surface of the eye, other than the retina, for providing a finite source of secondary radiation on the retina of the eye, which secondary radiation is emitted from the retina as a reflected wavefront of radiation that passes through the eye.

40. The method according to claim 39, wherein the optical beam focusing includes focusing the optical beam on the anterior surface of the cornea.

41. The method according to claim 39, further comprising projecting the reflected wavefront onto a wavefront analyzer and measuring differences between the reflected wavefront and a desirable wavefront.

42. The method according to claim 39, further comprising generating a linearly polarized, collimated beam of light and positioning a long focal length lens for directing the collimated beam of light through the long focal length lens, wherein the focusing includes converging the collimated light through a small angle to a focal point on the anterior surface of the eye.

43. The method according to claim 42, wherein the linearly polarized collimated beam comprises a laser beam.

44. The method according to claim 39, further comprising viewing the size of the finite secondary radiation source on the retina, and varying anterior surface focus locations for selecting a desired size of the source.

45. A method for measuring optical characteristics of an optical system, the method comprising the steps of:
focusing an optical beam proximate an anterior surface of the optical system for placing a finite source of secondary radiation on a focal surface of the optical system, wherein the anterior surface is other than the focal surface, which secondary radiation is emitted from the focal surface as a reflected wavefront of radiation that passes through the optical system;
projecting the reflected wavefront onto a wavefront analyzer; and
measuring characteristics of the optical system associated with the reflected wavefront.

46. The method according to claim 45, wherein the optical system comprises a human eye, and wherein the anterior surface is other than the retina and the focal surface comprises the retina of the eye.

47. The method according to claim 45, wherein the distortion measuring step comprises the step of comparing the reflected wavefront received by the wavefront analyzer to a desirable wavefront received by the wavefront analyzer.

48. The method according to claim 45, wherein the distortion measuring step comprises the step of determining an optical path difference between a plane wave and the wavefront emanating from the optical system.

49. The method according to claim 48, wherein the optical path difference results from a Zernike reconstruction of the wavefront.

50. The method according to claim 45, wherein the distortion measuring step comprises the steps of:
positioning an opaque plate having an aperture therein for transmitting a portion of the emitted wavefront therethrough;
placing a light sensitive material downstream of and in spaced relation to the opaque plate for receiving the portion of the reflected wavefront projected as a finite image onto a first position of the light sensitive material;
projecting the reflected wavefront onto the plate for placing a first finite image onto the light sensitive material;
projecting a desirable wavefront onto the plate for placing a second finite image at a second location on the light sensitive material; and
measuring a difference between the first position and the second position.

51. The method according to claim 50, wherein the aperture comprises an aperture array and wherein the light sensitive material comprises a CCD array.

52. The method according to claim 45, further comprising the step of converting the measured distortions to an optical correction based on a deviation of the reflected wavefront from a desirable wavefront.

53. The method according to claim 45, further comprising the steps of:
viewing the focal surface through a camera; and
selecting a desired size of the finite source of secondary radiation.

54. An apparatus for measuring vision characteristics of an optical system, the apparatus comprising:
focusing means for focusing an optical beam proximate an anterior surface of the optical system for providing a finite source of secondary radiation on a focal surface, which anterior surface is other than the focal surface, which secondary radiation is emitted from the focal surface as a reflected wavefront of radiation that passes through the optical system;
directing means for directing the reflected wavefront onto a wavefront analyzer; and a wavefront analyzer for measuring distortions associated with the reflected wavefront.

55. The apparatus according to claim 54, wherein the focusing means comprises a long focal length lens for converging the optical beam through a small angle and focusing the optical beam on the anterior surface.

56. The apparatus according to claim 55, wherein the long focal length lens has a focal length of at least one half meter in length.

57. The apparatus according to claim 54, wherein the focusing means comprises a zoom lens for converging the optical beam through a small angle and varying the focusing of the optical beam onto various anterior surfaces.

58. The apparatus according to claim 54, further comprising a laser for providing the optical beam.

59. The apparatus according to claim 54, further comprising the a shutter operable from a closed position to an open position for controlling an amount of optical beam energy delivered to the optical system.

60. The apparatus according to claim 54, wherein the wavefront analyzer comprises:
   an opaque plate having an aperture therein for transmitting a portion of the emitted wavefront therethrough; and
   a light-sensitive material downstream of and in spaced relation to the opaque plate for receiving the portion of the reflected wavefront projected as a finite image thereon.

61. The apparatus according to claim 60, wherein the aperture comprises an aperture array and wherein the light-sensitive material comprises a CCD array.

62. The apparatus according to claim 61, further comprising a lens carried within each of the plurality of apertures of the aperture array.

63. The apparatus according to claim 54, further comprising polarizing means for polarizing the optical beam.

64. The apparatus according to claim 63, further comprising a polarization beam splitter for reflecting an S-component of the reflected wavefront and for transmitting a P-component of the reflected wavefront as a polarized wavefront therethrough.

65. The apparatus according to claim 54, further comprising a camera positioned for viewing the focal surface.

66. An apparatus for measuring vision characteristics of an eye, the apparatus comprising:
   a laser for providing an optical beam;
   focusing means for focusing the optical beam on an anterior surface of the eye, other than the retina, for providing a finite source of secondary radiation on the retina of the eye, which secondary radiation is emitted from the retina as a reflected wavefront of radiation that passes outward from the eye;
   polarizing means placed within a path of the optical beam for transmitting a polarized wavefront therethrough; and
   a wavefront analyzer receiving the polarized wavefront for measuring distortions associated therewith.

67. The apparatus according to claim 66, wherein the focusing means comprises a long focal length lens for converging the optical beam through a small angle and focusing the optical beam on the anterior surface.

68. The apparatus according to claim 67, wherein the long focal length lens has a focal length of approximately one half meter in length.

69. The apparatus according to claim 66, further comprising the a shutter operable from a closed position to an open position for controlling an amount of optical beam energy delivered to the eye.

70. The apparatus according to claim 66, wherein the wavefront analyzer comprises:
   an opaque plate having an aperture therein for transmitting a portion of the emitted wavefront therethrough; and
   a light-sensitive material downstream of and in spaced relation to the opaque plate for receiving the portion of the reflected wavefront projected as a finite image thereon.

71. The apparatus according to claim 70, wherein the aperture comprises an aperture array and wherein the light-sensitive material comprises a CCD array.

72. The apparatus according to claim 71, further comprising a lens carried within each aperture of the aperture array.

73. The apparatus according to claim 66, further comprising a fixation target for viewing by a patient whose eye is being measured, the fixation target assuring that a patient whose eye is being measured is looking along a preferred direction.

74. The apparatus according to claim 66, further comprising a camera positioned for viewing the focal surface.

75. A method for measuring vision defects of an eye, the method comprising the steps of:
   focusing an optical beam proximal of the retina of the eye, but not on the retina, for placing a finite source of secondary radiation on the retina, which secondary radiation is emitted from the retina as a reflected wavefront of radiation that passes through the eye;
   projecting the reflected wavefront onto a wavefront analyzer; and
   measuring distortions associated with the reflected wavefront.

76. A method for measuring vision defects of an eye, the method comprising the steps of:
   focusing an optical beam proximate a retina of the eye, but not on the retina, for placing a finite source of secondary radiation on the retina, which secondary radiation is emitted from the retina as a reflected wavefront of radiation that passes through the eye;
   projecting the reflected wavefront onto a wavefront analyzer; and
   measuring distortions associated with the reflected wavefront.

* * * * *

UNITED STATES PATENT AND TRADEMARK OFFICE
CERTIFICATE OF CORRECTION

PATENT NO. : 6,270,221 B1
DATED : August 7, 2001
INVENTOR(S) : Liang et al.

It is certified that error appears in the above-identified patent and that said Letters Patent is hereby corrected as shown below:

Column 4,
Line 16, delete "or an eye" and insert -- of an eye --.

Column 5,
Line 28, delete "cornea ." and insert -- cornea. --.
Line 34, delete "approximate" and insert -- approximately --.

Column 7,
Line 14, delete "te" and insert -- the --.
Line 33, delete "te" and insert -- the --.
Line 34, delete "te" and insert -- the --.

Column 10,
Line 62, delete "patent" and insert -- patient --.

Signed and Sealed this

Twenty-sixth Day of February, 2002

Attest:

*Attesting Officer*

JAMES E. ROGAN
*Director of the United States Patent and Trademark Office*